United States Patent [19]

Reagan et al.

[11] Patent Number: 4,731,237
[45] Date of Patent: Mar. 15, 1988

[54] IMMUNE RESPONSE TO VIRUS INDUCED BY ANTI-IDIOTYPE ANTIBODIES

[75] Inventors: Kevin J. Reagan, Wycliffe, Del.; Tadeusz J. Wiktor; Hilary Koprowski, both of Wynnewood, Pa.

[73] Assignee: The Wistar Institute, Philadelphia, Pa.

[21] Appl. No.: 549,506

[22] Filed: Nov. 7, 1983

[51] Int. Cl.⁴ ..................... A61K 39/42; C12N 15/00; C12N 5/00
[52] U.S. Cl. ................................... 424/86; 435/172.2; 435/240.27; 935/95; 935/104; 935/107
[58] Field of Search ................. 435/172.3, 172.2, 240, 435/241; 424/85, 86, 88, 92; 260/112 R, 112 B

[56] References Cited

U.S. PATENT DOCUMENTS 4,172,124 10/1979 Koprowski ........................... 424/85
4,196,265 4/1980 Koprowski ........................... 424/85

FOREIGN PATENT DOCUMENTS

| 868099 | 10/1978 | Belgium . |
| 900023A | 10/1984 | Belgium . |
| 82789 | 6/1983 | European Pat. Off. . |
| 106615 | 4/1984 | European Pat. Off. . |
| 0110706 | 6/1984 | European Pat. Off. . |
| 0113431 | 7/1984 | European Pat. Off. . |
| 119629 | 9/1984 | European Pat. Off. . |
| 139389 | 5/1985 | European Pat. Off. . |
| 0142345 | 5/1985 | European Pat. Off. . |
| 3145007 | 5/1983 | Fed. Rep. of Germany . |
| 2819110 | 5/1985 | Fed. Rep. of Germany . |
| 02848 | 8/1984 | PCT Int'l Appl. . |
| 8404327 | 11/1984 | PCT Int'l Appl. . |
| 02909 | 7/1985 | PCT Int'l Appl. . |

OTHER PUBLICATIONS

Chemical Abstracts, vol. 97, 179920c, 1982.
Chemical Abstracts, vol. 100, 207644c, 1984.
Chemical Abstracts, vol. 100, 83892z, 1984.
Chemical Abstracts, vol. 101, 108793d, 1984.
Herlyn et al., "Colorectal Carcinoma-Specific Antigen: Detection by Means of Monoclonal Antibodies," Proc. Natl. Acad. Sci. USA 76, pp. 1438–1442, 1979.
Stevenson et al., "Treatment of Lymphoid Tumors with Anti-Idiotype Antibodies," Springer Seminars in Immunopathology 6, pp. 99–115, 1983.
Kozbor et al., "Human Hybridomas Constructed with Antigen-Specific Epstein-Barr Virus-Transformed Cell Lines," Proc. Natl. Acad. Sci. USA, vol. 79, pp. 6651–6655, 1982.
Haughton et al., "Antigen-Induced Murine B Cell Lymphomas II. Exploitation of the Surface Idiotype as Tumor Specific Antigen," The Journal of Immunology, vol. 121, No. 6, pp. 2358–2362, 1978.
Thielemans et al., "Strategies for Production of Monoclonal Anti-Idiotype Antibodies Against Human B Cell Lymphomas," The Journal of Immunology, vol. 133, No. 1, pp. 495–501, 1984.
Kim et al., "Polyvalent Epitope Inhibits but Added with Anti-Idiotype Antibody Enhances Idiotype Suppression," The Journal of Immunology, vol. 131, No. 1, pp. 13–15, 1983.
Forstrom et al., "Immunization to a Syngeneic Sarcoma by a Monoclonal Auto-Anti-Idiotypic Antibody", Nature, vol. 303, pp. 627–629, 1983.
Gheuens et al., "Idiotypes and Biological Activity of Murine Monoclonal Antibodies Against the Hemagglutinin of Measles Virus," Infection and Immunity, vol. 34, No. 1, pp. 200–207, 1981.
Metzger, "A Mouse Monoclonal Antibody Against Rabbit $V_H$ Allotype Shares the Predominant Idiotype with a Rabbit Antibody of the Same Specificity," Eur. J. Immunol., vol. 14, pp. 304–308, 1984.
Kauffman et al., "Cell Receptors for the Mammalian Reovirus II. Monoclonal Anti-Idiotypic Antibody Blocks Viral Binding to Cells," J. of Immunology, vol. 131, No. 5, pp. 2539–2541, 1983.
Noseworthy et al., "Cell Receptors for the Mammalian Reovirus I. Syngeneic Monoclonal Anti-Idiotypic Antibody Identifies a Cell Surface Receptor for Reovirus," J. of Immunology, vol. 131, No. 5, pp. 2533–2538, 1983.
Ionescu-Matiu et al., "Epitopes Associated with a Synthetic Hepatitis B Surface Antigen Peptide," J. of Immunology, vol. 130, No. 4, pp. 1947–1952, 1983.
Kennedy et al., "Inhibition of a Common Human Anti--Hepatitis B Surface Antigen Idiotype by a Cyclic Synthetic Peptide," Journal of Virology, vol. 46, No. 2, pp. 653–655, 1983.
Urbain, Springer Seminars in Immunopathology, vol. 6, pp. 1–5, 1983.
Eichmann et al., "Network Regulation Among T Cells; Conclusions from Limiting Dilution Experiments," Springer Seminars in Immunopathology, vol. 6, pp. 7–32, 1983.
Goldman et al., "Pathological Expression of Idiotypic Interactions: Immune Complexes and Cryoglobulins," Springer Seminars in Immunopathology, vol. 6, pp. 33–49, 1983.
Roitt et al., "Idiotypes and Autoimmunity", Springer Seminars in Immunopathology, vol. 6, pp. 51–66, 1983.
Strosberg, "Anti-Idiotype and Anti-Hormone Receptor Antibodies," Springer Seminars in Immunopathology, vol. 6, pp. 67–78, 1983.
Rodkey, "Autoregulation of Immune Responses via Idiotype Network Interactions," Microbiological Reviews, vol. 44, pp. 631–659, 1980.

(List continued on next page.)

Primary Examiner—Blondel Hazel
Attorney, Agent, or Firm—Banner, Birch, McKie & Beckett

[57] ABSTRACT

A method of inducing an immunological response in a host to a virus is provided employing anti-idiotype antibodies that present an internal image of a viral antigen to the host. Anti-idiotype antibodies and the cell lines that produce such antibodies are also provided.

13 Claims, No Drawings

OTHER PUBLICATIONS

Nisonoff et al., "Hypothesis Implications of the Presence of an Internal Image of the Antigen in Anti-Idiotypic Antibodies: Possible Application to Vaccine Production," Clinical Immunology and Immunopathology, vol. 21, pp. 397–406, 1981.

Sacks et al., "Induction of Immune Responses with Anti-Idiotypic Antibodies: Implications for the Induction of Protective Immunity," Springer Seminars in Immunopathology, vol. 6, pp. 79–97, 1983.

Reagan et al., "Anti-Idiotypic Antibodies Induce Neutralizing Antibodies to Rabies Virus Glycoprotein," Journal of Virology, vol. 48, pp. 660–666, 1983.

Koprowski et al., "Human Anti-Idiotype Antibodies in Cancer Patients; Is the Modulation of the Immune Response Beneficial for the Patient?", Proc. Natl. Acad. Sci. USA, vol. 81, pp. 216–219, 1984.

Kennedy et al., (1984) *J. Exp. Med.* 159:655–665.

Kennedy et al., (Aug. 1983) *Science* 221:853–855.

Kennedy et al., (1984) *J. Virol.* 50:951–953.

Sacks et al., (1982) *J. Exp. Med.* 155:1108–1119.

Nepom et al. (1984) *Proc. Natl. Acad. Sci. USA* 81:2864–2867.

Eichmann et al., (1975) *Eur. J. of Immunol.* 5:661–666.

Geha, (1981), *N. Engl. J. Med.* 305:25–28.

Eichmann, (1974) *Eur. J. of Immunol.* 4:296–301.

Bona et al., (1981) *J. Exp. Med.* 153:951–967.

Sege et al. (1978) *Proc. Natl. Acad. Sci USA* 75:2443–2447.

Nepom et al. (1982) *J. Exp. Med.* 155:155–167.

IMMUNE RESPONSE TO VIRUS INDUCED BY ANTI-IDIOTYPE ANTIBODIES

TECHNICAL FIELD

The present invention is directed to the induction of an immunological response to a virus. More specifically, the present invention is directed to a method of using anti-idiotype antibodies to induce an immune response to a virus, as well as antibodies and cell lines useful in such a method.

BACKGROUND OF THE INVENTION

The sequence of amino acids in the variable regions of both heavy ($V_H$) and light ($V_L$) chains of immunoglobulin (Ig) produces a conformation in the antigen binding site (i.e., parotope) allowing interaction of that antibody with a specific antigen. Injection of $I_g$ into heterologous host animal will give rise to anti-xenotypic (specific for species), anti-isotypic (specific for Ig class), and anti-idiotypic (specific for antibody vairable region) antibodies. Two functional classes of anti-idiotypic antibodies can exist, one of which reacts with the praotope, and another which reacts with the $V_H$ and/or $V_L$ framework (framework determinants). See generally, Geha, (1981) *N. Engl. J. Med.* 305:25-28; Jerne, (1974) *Ann. Immunol.* (Paris) 125C: 373-389.

SUMMARY OF THE INVENTION

It is an object of the present invention to provide a method of inducing an immunological response in a mammal to a virus, such as rabies virus.

It is also an object of the present invention to provide a method of producing an immunological response to a virus that employs anti-idiotype antibodies.

Another object of the present invention is to provide a method of immunizing a patient against a virus such as rabies virus that limits the number of inoculations with viral vaccine.

Yet another object of the present invention is to provide antiidiotype antibodies and cell lines that produce such antibodies that are useful in a method of inducing an immunological response to a virus.

These and other objects of the present invention are achieved by one or more of the following embodiments.

In one embodiment, the present invention provides a method of inducing an immunological response to rabies virus comprising: (a) providing an anti-idiotype antibody, an epitope identified by said antiidiotype antibody being the parotope of an anti-virus antibody; and (b) stimulating in a mammal the production of anti-(anti-idiotype) antibodies that identify an epitope on a virus particle by administering said anti-idiotype antibody to said mammal.

In another embodiment, the present invention provides an immortal B lymphocyte that produces an anti-idiotype antibody, an epitope identified by said anti-idiotype antibody being the parotype of an antivirus antibody. The present invention also contemplates the monoclonal antibodies produced by such an immortal B lymphocyte substantially free of other antibodies.

In still another embodiment, the present invention provides polyclonal anti-idiotype antibodies, an epitope identified by said antiidiotype antibodies being the parotope of an anti-virus antibody, substantially free of anti-isotype antibodies.

Yet another embodiment of the present invention provides a method of inducing an immunological response to rabies virus comprising: (a) providing an anti-idiotype antibody that identifies an epitope in the variable region of an anti-rabies virus antibody; and (b) administering anti-idiotype antibody to a mammal, said mammal thereby being stimulated to produce anti-(anti-idiotype) antibody that recognizes an epitope on a rabies virus particle.

DETAILED DESCRIPTION OF THE INVENTION

The present invention provides an approach to immunization against viruses, significantly different than the traditional approach of immunization with conventional vaccines. Applicants have discovered that an immunological response to a virus can be induced in a host by administering to the host an antibody that is anti-idiotype to an antivirus antibody. The induction of this response has utility as a preventive or therapeutic treatment.

Although applicatns do not wish to be bound by any particular theory of operabilty, it is believed that the observed immunological response achieved by the present invention is attributable to an interaction between the anti-idiotype antibody molecules and the host mammal's immune system. The idiotypic (or i.e., variable) region of the anti-idiotype antibody molecule contains antigenic determinants (i.e., epitopes) seen as antigens by the host. This induces the production of anti-(anti-idiotype) antibodies by the host. Within this set of anti(anti-idiotype) antibodies are those that are directly complimentary to the parotope of the anti-idiotype antibody. It is further believed that the parotope of the anti-idiotype antibody presents an "internal" image of the virus epitope identified (i.e., selectively bound) by the idiotype antibody and, therefore, the anti-(anti-idiotype) antibodies will also bind the antigen on the virus particle. In effect, the present method induces an immunological response to the virus by presenting an antigen (the parotope of the anti-idiotype antibody) which is essentially indistinguishable from the viral antigen to a portion of the host's resulting antibodies.

Surprisingly, the above method has been found to be an effective way of inducing an immunological response to a virus. The present invention contemplates the induction of an immunological response to any virus, such as influenza, herpes simplex and hepatitis viruses, but will be described below for illustrative pruposes in terms of rabies virus. It is not, however, intended to limit the scope of the invention thereby.

The idiotype of an antibody is defined by individually distinctive antigenic determinants in the variable or idiotypic region of the antibody molecule. A portion of these idiotypic determinants will be on or closely associated with the parotope of the antibody, while others will be in the framework of the variable region. While each antibody has its own idiotype, particular antibodies will be referred to below by the following terms. "Idiotype antibody" or "Id Ab" refers to an anti-virus antibody (i.e., the epitope identified by the idiotype antibody is on a rbies virus particle). "Anti-idiotype antibody" or "anti-Id Ab" refers to an antibody which identifies an epitope in the variable region of an idiotype antibody. A portion of such antibodies will identify an epitope that is the parotope of the idiotype antibody, thus presenting an "internal" image of the epitope detected by the idiotype antibody on the virus particle. "Anti-(anti-idiotype) antibody (or anti-)anti-Id)Ab" is an antibody that identifies an epitope in the variable region of the anti-idiotype antibody. A portion of the anti(anti-idiotype) antibodies will detect an epitope that corresponds to (i) the parotope of the anti-idiotype antibody, and (ii) an epitope on a virus particle.

As stated below, the method of the present invention contemplates administering anti-idiotype antibody to a host. The anti-idiotype antibody is administered to the host in an yphysiologically suitable carrier (e.g., sterile, pyrogen-free physiological saline), the formulations of which are within the skill of the art. The selection of carrier is not critical and the antibody can be administered by any method that introduces the antibody into the circulatory system (e.g., intravenous, intramuscular or subcutaneous injection).

The host can be any mammal, but most commonly a human, dog or cat. The amount of antibody administered to a host can vary widely dependent, for example, upon the particular antibody employed and the host inoculated. It is only necessary that sufficient antiidiotype antibody be administered to the host to stimulate the production of anti-(anti-idiotype) antibodies by the host's immune system. The amounts of antibody employed, however, need not be very great because only very small amounts are necessary to induce an immunological response. In many cases, a dosage of anti-idiotype antibody within the range of a few micrograms to a few milligrams should be sufficient (e.g., about 50–200 up to about 1–5 mg). The determination of an appropriate dosage is readily with in the skill of the art.

The present invention effects an immune response by administering a formulation containing an anti-idiotype antibody to a host wherein the parotope of the anti-idiotype antibody is an internal image of a virus antigen. Such an antibody recognizes an epitope that is the parotope of the corresponding idiotype antibody. Anti-idiotype antibodies that present internal images of the viral antigen can be distinguished from anti-idiotype antibodies that recognize framework determinants in the variable region of the idiotype antibody by several methods. One method of identifying the desired anti-idiotype antibodies is a competitive binding assay between the viral antigen (or hapten if available), the idiotype antibody and the anti-idiotype antibody. If the viral antigen blocks binding of the anti-idiotype antibody to the idiotype antibody, the epitope identified by the antiidiotype antibody is closely associated with the idiotype antibody's parotope. Another test is to determine if antisera to the antiidiotype antibody is also anti-virus. These and other methods of identifying the appropriate anti-idiotype antibody are within the skill of the art. In the formulation administered to a host, the inclusion of anti-idiotype antibodies directed to framework determinants along with the subclass of anti-idiotype antibodies directed to the idiotype antibody's parotope is acceptable. It is only necessary that the antiidiotype antibody formulation contain the subclass directed to the idiotype antibody's parotope.

The anti-idiotype antibody employed can be homologous or heterologous to the host. It may be desirable, however, to employ human antibody if the host is human to minimize anti-xenotypic reactions. This is not essential because, as noted above, only relatively minor amounts of anti-idiotype antibody are employed. In the absence on any seriour reaction to heterologous anti-idiotype antibody, heterologous antibody may be preferred due to ease and cost of preparation. Furthermore, the anti-idiotype antibody can be either polyclonal or monoclonal antibody.

Polyclonal anti-idiotype antibody can be prepared by conventional methods known in the art. For example, polyclonal anti-Id Ab can be produced by 8immunizing an animal with a monoclonal anti-rabies virus antibody (i.e., Id Ab). The immunized animal will produce anti-Id Ab. A subclass of this anti-idiotype antibody in the anti-sera will detect an epitope that is the parotope of the anti-rabies virus anitbody. Anti-sera collected from the animal can be purified, for example, by sequential absorbtion with (i) an immobilized anitbody of the same isotype as the monoclonal Id Ab, but different idiotype, to remove anti-isotypic antibodies from the anti-sera, and (ii) the immobilized monoclonal Id Ab to removal the anti-Id Ab, a subclass of which will present internal images of the viral antigen. The anti-Id Ab is then eluted from the bound monoclonal anti-rabies virus antibody to provide a solution substantially free of anti-isotype antibodies. This solution can then be tested for the presence of anti-Id Ab that detects the parotope of the Id Ab. This method, as well a others within the skill of teh art, is generally applicable in the preparation of anti-Id Ab for any viral anti-Ib Ab.

Monoclonal anti-idiotype antibodies substantially free of other antibodies can be isolated from the supernatant of a substantially pure culture of immortal B lymphocytes. The tem "immortal B lymphocyte" encompasses any relatively stable, continuous antibody-producing cell that can be maintained in culture for several months (preferably indefinitely), such as hybridomas (somatic cell hybrids of normal and malignant lymphocytes) and normal lymphocytes transformed by virus (e.g., Epstein-Barr virus) or oncogenic DNA. The production of immortal B lymphocytes from normal B lymphocytes that produce anti-idiotype antibody is within the skill of the art. See, e.g., Gerhard et al., (1978) *Proc. Natl, Acad. Sci.* USA 75 1510–1514; *Monoclonal Antibodies* (R. H. Kennett, T. J. McKearn & K. B. Bechtol 1980); M. Schreier et al., *Hybridoma Techniques* (Cold Spring Harbor Laboratory 1980); *Monoclonal Antibodies and T-Cell Hybridomas* (G. J. Hammerling, U. Hammerling & J. F. Kearney 1981); Kozbor et al., (1982) *Proc. Natl. Acad. Sci* USA 89: 6651–6655; Jonak et al., (1983) *Hybridoma* 2:124; *Monoclonal Antibodies and Functional Cell Lines* (R. H. Kennett, K. B. Bechtol & T. J. McKearn 1983); Kozbor et al., (1983) *Immunology Today* 4: 72–79.

Normal B lymphocytes producing anti-Id Ab and suitable for the production of an immortal B lymphocyte can be provided by various methods within the skill of the art. For example, an animal, such as a rat or mouse, can be immunized with a monoclonal anti-virus antibody and B lymphocytes producing anti-Id Ab recovered from the animal's spleen. Human B lymphocytes producing anti-Id Ab can be obtained by immunizing a patient with monoclonal anti-virus antibody, collecting peripheral bloom lymphocytes from the patient, and then inducing in vitro the growth of B lymphocytes producing anti-Id Ab by stimulating the in vitro culture with the monoclonal anti-virus antibody. See, e.g., DeFreitas et al., (1982) *Proc. Natl. Acad. Sci.* USA 79:6646–6650. The animal or human B lymphocytes producing anti-Id Ab can thus be recovered and immortalized by those of skill in the art. Of course it is understood that those lymphocytes producing antiId Ab that present internal images of the virus antigen should be distinguished from B lymphocytes producing anti-Id Ab directed to framework determinants in the idiotypic region.

If desired, the immune response produced in the host mammal to a virus can be further heightened by immunization with a conventional virus vaccine in addition to the administration of anti-Id Ab as described above. After the production of anti-(anti-Id) Ab is stimulated in the host mammal by administering anti-Id Ab (e.g., about 2 weeks post-administration), the host is then given one inoculation of a virus vaccine employing conventional techniques known in the art (e.g., killed virus vaccines such as HDC rabies vaccine). See, Plotkin et al., (1976) *Am. J. Epidemiology* 103:75–80; Wiktor et al., *Rabies Vaccine for Human Use: Volume* 40, pp. 3–9 (1978). The types of vaccine and protocols for their administration are within the skill of the art.

The following experimental examples are provided for illustrative purposes only and are not intended to limit the scope of the present invention.

Preparation of Anti-Idiotype Antibody

The ability of anti-idiotype antibody (anti-Id Ab) made against various monoclonal antibodies (mAb) to reconstruct the epitopes of rabies virus glycoprotein (G) was studied. This G is responsible for many of the important biological properties of rabies virus, including the induction of the virus-neutralizing antibodies (VNA). Precisely which portion of the G is responsible for this function is now known at present. A function epitope map for challenge virus standard (CVS) strain of rabies virus G suggesting the existance of at least three major antigenic sites for type-specific VNA has been described in Lafon et al., (1983) *J. Gen. Virol.* 64:843–851.

Five anti-g mAb were selected from a large panel of hybridomas on the basis of their isotype (enabling purification by protein A-Sepharose chromatography) and binding site on the rabies virus G as defined by the functional epitope map. Anti-rabies virus G mAb's 509-6, 101-1, 507-1 and 719-3 have been described previously. Lafon et al., supra: Wiktor et al., (1980) *J. Exp. Med.* 152:99–112. These mAb, which strongly neutralize rabies virus infectivity, have the following characteristics: 509-6 (epitope map site I; IgG2a), 101-1 (epitope map site IIb; IgG2a), 507-1 (epitope map site IIIb; IgG1), and 719-3 (epitope map site IIc; IgG2a). Anti-g mAb 1104-2 (IgG1) was obtained from an additional fusion of splenocytes from rabies virus immunized BALB/c mice with the 653 variant of P3x63Ag8 mouse myeloma cells, Kearney et al., (1979(*J. Immunol.* 123:1548–1550, as described in Wiktor et al., (1978) *Proc. Natl. Acad. Sci.* USA 75:3938–3942. The anti-G-secreting hybridoma cells were selected, cloned by limiting dilution, and ascites fluids prepared as also described in Wiktor et al., (1978), supra. The 1104-2 mAb was selected because it demonstrated excellent binding to ERA virus, but poor neutralization. Anti-rabies virus nucleoapsid mAb 515-3 (IgG2a) and 389-1 (IgG1) were isolated by similar techniques from Kelev virus-immunized BALB/c mice.

The stock of ERA or CVA strains of rabies virus employed were propagated in BHK-21 cells by standard methods. See Wiktor et al., in *Laboratory Techniques in Rabies*, pp. 101–123 (M. Kaplan & H. Koprowski 3rd ed. 1973). Rabies antigenic variants, ERA RV194-2 and RV 509-6, have been described and represent viruses which are resistance to neutralization by anti-G mAb 194-2 and 509-6, respectively. See Dietzschold et al., (1983) *Proc. Natl. Acad. Sci.* USA 80: 70-74. Rabies soluble glycoprotein ($G_s$) was pruified from virion-depleted culture fluids by immunoadsorbent chromotography as described in Dietzschold et al., (1983) *Virology* 124: 330–337.

All anti-G mAb were purified from ascites fluids. Antibodies of the IgG2a isotype were diluted approximately 1:30 with Britton-Robinson buffer (BRB) at pH 8.0. See Gerhard et al., in *Monoclonal Antibodies*, pp. 317–333 (R. Kennett, T. McKearn 7 K. Bechtol 1980). The mAb in BRB was passed through a Nalgene 0.45 $\mu$ filter, and then over a protein A-Sepharose 4B absorption column (Pharmacia, Piscatawy, N.J.). The column was washed with 30 ml of BRB, pH 8.0, before antibody was eluted with BRB at pH 3.0. Anti-G mAb of IgG1 isotype were first precipitated with sodium sulfate at a final concentration of 18% (w/v). The Ig fraction was dissolved and dialyzed in BRB, pH 8.0, and then passed over the protein A-Sepharose column as before. Ig eluted from the column was detected by radioimmunoassay (RIA) using ERA virus as antigen. See, Dietzschold et al., (1982) *J. Virol.* 44: 595–602. Antibodies were concentrated by vacuum dialysis against phosphate-buffered saline, pH 7.4 (PBS). Protein concentration was determined using bovine serum albumin as a standard. See Bramhall et al., (1969) *Anal Biochem.* 31: 146–148.

Anti-Id Ab were prepared as described in Staudt et al., (1983) *J. Exp. Med.* 157: 687–704. Briefly, female New Zealand white rabbits were injected subcutaneously in multiple sites along the mammary chain with 300 ug of protein A-Sepharose-purified mAb emulsified in Freund's complete adjuvant (FCA). Two intramuscular boosters of 100 $\mu$g of antibody in PBS were given on days 7 and 30, and sera are collected 10 days later. Each anti-idiotypic anti-serum was made specific for idiotype regions by passage over a Sepharose 4B column to which either mAb 515-3 (IgG2a) or 389-1 (IgG1) were coupled to remove anti-isotype Ab. The effluent from such columns contained the antibodies reactive with idiotype determinants. Antibodies to constant regions were eluted from the mAb 515-3 and 389-1 immunoadsorbent columns with 0.1 M diethylamine, pH 11.5. IgG from each anti-Id Ab was isolated by protein A-Sepharose chromatography as above. The reactivity of the column effluent with non-idiotypic determinants was neglegible.

Characterization of Anti-Isiotype Antibodies

The specificity of the anti-Id Ab prepared above and the existence of cross-reactive idiotypes among the various anti-G mAb was determined for each anti-Id Ab preparation in a RIA.

A solid phase RIA was used to measure the bidnings of anti-Id Ab to fixed mAb. Individual mAb were diluted depending on the ascites fluid concentration in carbonate-bicarbonate buffer, pH 8.9, as follows: 509-6 (1:3,000), 101-1 (1:6,000), 719-3 (1:6,000), 507-1 (1:6,000), 1104-2 (1:16,000). Then 25 $\mu$l of each was added to wells of polyvinyl microtiter plates (Dynatech Laboratories). These antibodies were allowed to dry to the wells by overnight incubation at 37° C. Free binding sites on the wells were blocked for at least 1 hour with 10% agamma horse serum (GIBCO Laboratories) in PBS with 0.08% sodium azide (PBSN). Twenty-five microliters of dilution of anti-Id Ab was added, and after 1 hour at room temperature, the plates were washed extensively. Bound anti-Id Ab was detected by adding 25 μl (30,000 cpm) of $^{125}$I goat anti-rabbit IgG (Cappel Laboratories) labeled by the iodogen method and incubating for an additionl hour at room temperature. See Markwell et al., (1978) Biochemistry 17: 4807–4817. All dilutions of anti-Id Ab or radiolabeled probe were made in 10% agamma horse serum in PBSN. Plates were washed free of unbound probe and radioactivity bound to individual wells were measured in a gamma counter.

The results of titrating each anti-Id Ab preparation against homologous and heterologous mAb demonstrated that each anti-Id Ab was specific for its homologous Id mAb.

Determination of Anti-Idiotype Antibodies Directed to the Parotope of the Idiotype Antibody A competition RIA was deviced to test the ability of rabies virus G to prevent the interaction between Id Ab and anti-Id Ab. See, Chaflin et al., (1974) J. Immumol. 112:1747–1756; Sher et al., (1972) J. Immunol. 109:176–178.

The rabies $G_S$ was used as the competing antigen. Pretitrated levels of mAb were incubated with serial two-fold dilutions of $G_S$ for 1 hour prior to the addition of a standardized anti-Id Ab dilution. The amount of bound anti-sera was determined by the binding of a $^{125}$I-labeled goat anti-rabbit antibody probe. The binding of three of the five anti-Id Ab to their corresponding anti-G mAb (509-6, 507-1 and 1104-2) was inhibited by $G_S$. Maximum inhibition varied from 20–50% with as much as 6 μp/ml $G_S$, but at least a 15% reduction was observed with as little as 0.75 μg/ml $G_S$. The inability to totally inhibit binding of anti-Id Ab was an indication that both framework and parotope site specificities were present in the three polyclonal anti-Id sera. This was confirmed by a Western blot analysis of anti-Id Ab reactivity with mAb which had been resolved by sodium dodecyl sulfate-polyacrylamide gel electrophoresis (SDS-PAGE) under reducing and non-reducing conditions. Sine the antigen-combining site is eliminated by reduction of mAb, the reactivity of anti-Id Ab with reduced mAb showed a specificity for framework determinants. The absence of any significant binding inhibition of $G_S$ for anti-Id Ab or anti-Id 719-3 Ab, suggests a minor or absent population or parotope specificities in these sera.

Preparation of Anti-(Anti-Idiotype) Antibody

The following examples demonstrates that anti-Id Ab reactive with the antigen-combining site of anti-G mAb contains a subpopulation which mimics the viral epitope recognized by these anti-G mAb and can induce an immunological response to G.

ICR mice in groups of 4 were inoculated subcutaneously with 40 μg/mouse of protein A-Sepharose-purifed anti-Id IgG emulsified in FCA. Subcutaneous booster inoculations were administered on days 7 and 32; each with 40 μg of anti-Id IgG in Freund's incomplete adjuvant. Five days following the last booster inoculation, animlas were bled via the retro-orbital plexus and pooled sera checked for rabies virus-neutralizing antibody (VNA). As a control, another group of mice received an immunization of protein A-Sepharose-purified normal rabbit IgG.

The levels of VNA in immunized mice were determined by a modification of the rapid fluorescence focus inhibition test. See Smith et al, in *Laboratory Techniques in Rabies*, pp. 354–357 (M. Kaplan & H. Koprowski 3rd ed. 1973). Serial two-fold dilutions of mouse serum were prepared in Microtite II plates (Falcon Plastics) (50 μl/well) and incubated for 1 hour at 37° C. with an equal volume of virus, containing $10^4$ PFU/50 μl. Following incubation, 50 μl of freshly trypsinized BHK-21 cells ($2 \times 10^6$ cells/ml) were added to each well, mixed, and 10 μl aliquots of the serum-virus-cell mixture were transferred (in duplicate) into wells of Terasaki plates (Falcon Plastics). After 20 hour incubation, plates were first rinsed with PBS and then with 80% (v/v) acetone in distilled water, and fixed for 30 min in 80% acetone at room temperature. Plates were dried and cells were stained for 30 min at 37° C. with 5 μl/well of fluorescein-conjugated anti-rabies nucleocapsid antibody of rabbit origin. See Wiktor, (1974) *Symp. Series Immunobiol. Standard* 21: 102–118. The control wells (containing virus but no antibody) shows approximately 40% of cells containing rabies virus-specific inclusions. The end point of virus neutralization was defined as the reciprocal of the highest serum dilution capable of reducing the number of rabies virus-infected cells by 505%.

The results of the rapid fluorescent focus inhibition trest is shown in the table below. Significant VNA titers were generated against ERA strain rabies virus in mice immunized with anti-Id 509-6 Ab, and with anti-Id 1104-2 Ab. The three other anti-(anti-Id) Ab failed to neutralize ERA virus. Control experiments showed that mouse anti-(normal rabbit IgG) Ab as well as the anti-Id Ab used for immunization, had no rabies virus neutralizing activity. Furthermore, preincubation of anti-(anti-Id 509-6) sera with anti-Id 509-6 Ab removed the neutralizing activity. Preincubation with normal rabbit serum, however, did not.

In order to get the specificity of the VNA generated, other rabies viruses were used in the neutralization assay. The CVS strain of rabies virus bound both mAb 509-6 and 1104-2 (data not shown), and the Table shows that CVS was neutralized by both anti-(anti-Id 509-6) sera and anti-(anti-Id 1104-2) sera. On the other hand, a variant of ERA virus, RV 509-6, which possessed a mutation in the 509-6 epitope resulting in the loss of binding or neutralizing activity by mAb 509-6, see Laton et al., (1983) J. Gen. Virol. 64: 843–852, was not neutralized by anti-(anti-Id 509-6) sera. Another neutralization-resistant variant, RV 194-2, was effectively neutralized by anti-(anti-Id 509-6) sera. Previous results demonstrated that the antigenic sites recognized by anti-G mAb 509-6 and 194-2 are totally independent. See Laton et al., supra. These data show that anti-(anti-Id 509-6) sera reacts solely with the epitope which is recognized by anti-G mAb 509-6, and thus this epitope has been simulated by anti-Id 509-6 Ab.

| | Neutralization of Rabies Virus Strains by Anti-(anti-Id) Serum | | | |
|---|---|---|---|---|
| | ERA | | | CVS |
| Mouse antiserum to: | Parent | RV 509-6 | RV 194-2 | Parent |
| Normal rabbit IgG | 4 | 4 | 4 | 4 |
| anti-Id 509-6 | 32 | 4 | 64 | 64 |
| anti-Id 101-1 | 4 | ND* | ND | ND |
| anti-Id 179-3 | 4 | ND | ND | ND |
| anti-Id 507-1 | 4 | ND | ND | ND |
| anti-Id 1104-2 | 128 | 4 | 128 | 64 |

-continued

Neutralization of Rabies Virus Strains by Anti-(anti-Id) Serum

| | ERA | | | CVS |
|---|---|---|---|---|
| Mouse antiserum to: | Parent | RV 509-6 | RV 194-2 | Parent |
| RIG** | 16 | 16 | 32 | 32 |

† The reciprocal of the highest dilution of serum capable of reducing the number of infected cells by 50% was taken as the neutralization titer.
*Not done.
**Human anti-rabies Ig was diluted to 0.2 international units per ml, and serial two-fold dilutions incubated with rabies virus.

While the invention has been described above in terms of several specific embodiments, these have been provided for illustrative purposes only and are not to limit the scope of the invention which is defined solely by the claims.

We claim:

1. A method of inducing an immunological response to a rabies virus comprising:

(a) providing an anti-idiotype antibody, an epitope identified by said anti-idiotype antibody being the parotope of an anti-rabies virus antibody; and (b) stimulating in a mammal the production of anti(anti-idiotype) antibodies that identify an epitope on a rabies virus particle by administering said anti-idiotype antibody to said mammel.

2. The method of claim 1 wherein said mammal is a human.

3. The method of claim 2 wherein said anti-idiotype antibody is a human monoclonal antibody.

4. The method of claim 1 wherein said mammal is selected from the group consisting of dogs and cats.

5. The method of claim 1 wherein said anti-idiotype antibody is a monoclonal antibody.

6. The method of claim 4 wherein said anti-idiotype antibody is a monoclonal antibody.

7. The method of claim 5 wherein said monoclonal antibody is selected from the group consisting of rat and mouse antibodies.

8. The method of claim 6 wherein said monoclonal antibody is selected from the group consisting of rat and moust antibodies.

9. The method of claim 1 further comprising the step of:

(c) immunizing said mammal with a rabies virus vaccine.

10. Polyclonal anti-idiotype antibodies, the epitope identified by said anti-idiotype antibodies being the parotope of an anti-rabies virus antibody, substantially free of anti-isotype antibodies.

11. An immortal B lymphocyte that produces an anti-idiotype antibody, the epitope identified by said anti-idiotype antibody being the parotope of an anti-rabies virus antibody, wherein said B lymphocyte has been immortalized by fusion with a malignant lymphocyte to produce a hybridoma.

12. The immortal B lymphocyte of claim 11 wherein said anti-idiotype antibody is selected from the group consisting of human, mouse and rat antibodies.

13. The monoclonal antibodies produced by the immortal B lymphocyte of claim 11 substantially free of other antibodies.

* * * * *